United States Patent
Dunbar et al.

(10) Patent No.: US 9,675,819 B2
(45) Date of Patent: Jun. 13, 2017

(54) HUMAN INTERFACE AND DEVICE FOR ULTRASOUND GUIDED TREATMENT

(71) Applicant: Mirabilis Medica, Inc., Bothell, WA (US)

(72) Inventors: Lee David Dunbar, Loon Lake, WA (US); Jessica E. Parsons, Seattle, WA (US); Robert H. Pedersen, Woodinville, WA (US); Tim Etchells, Seattle, WA (US); Gregory Paul Darlington, Snohomish, WA (US); Michael P. H. Lau, Edmonds, WA (US); Jens Ulrich Quistgaard, Seattle, WA (US)

(73) Assignee: Mirabilis Medica, Inc., Bothell, WA (US)

( * ) Notice: Subject to any disclaimer, the term of this patent is extended or adjusted under 35 U.S.C. 154(b) by 0 days.

(21) Appl. No.: 13/943,747

(22) Filed: Jul. 16, 2013

(65) Prior Publication Data

US 2014/0018708 A1 Jan. 16, 2014

Related U.S. Application Data

(60) Provisional application No. 61/672,213, filed on Jul. 16, 2012, provisional application No. 61/798,831, filed on Mar. 15, 2013.

(51) Int. Cl.
*A61N 7/00* (2006.01)
*A61N 7/02* (2006.01)
(Continued)

(52) U.S. Cl.
CPC ............... *A61N 7/00* (2013.01); *A61B 34/25* (2016.02); *A61N 7/02* (2013.01); *A61B 2090/378* (2016.02)

(58) Field of Classification Search
CPC .. A61N 7/00; A61N 7/02; A61B 19/56; A61B 2090/378; A61B 34/25
(Continued)

(56) References Cited

U.S. PATENT DOCUMENTS 6,488,626 B1    12/2002  Lizzi
8,282,554 B2 *  10/2012  Makin .................. A61B 8/4281
                                                    600/437
(Continued)

FOREIGN PATENT DOCUMENTS

WO    WO 2009044316 A1 *  4/2009

OTHER PUBLICATIONS

Khurana, Ashok, "3D/4D Ultrasound in Gynecology," Apr.-Jun. 2010, Donald School Journal of Ultrasound in Obstetrics and Gynecology, 4(2):127-155.*
(Continued)

*Primary Examiner* — Long V Le
*Assistant Examiner* — Katherine McDonald
(74) *Attorney, Agent, or Firm* — Seed IP Law Group LLP

(57) ABSTRACT

A system and method for providing real-time, image-guided high intensity focused ultrasound (HIFU) targeting and treatment of tissue. In one embodiment, the system includes an HIFU applicator and a user interface with a touchscreen display for three-dimensional visualization of the tissue. Image frames displayed on the user interface depict real-time images of the tissue, including an image parallel to a feature of the applicator and an image orthogonal to the parallel image. Reference lines may be sketched using the touchscreen and displayed on the image frames. In one embodiment, tissue boundaries are detected and marked on the image frames, either by the user or automatically by the system. In another embodiment, the user interface includes a footswitch for the user to interact with the system. In another embodiment, the system includes an ultrasound
(Continued)

imaging component configured to undock from the system for use as a stand-alone ultrasound imaging device.

20 Claims, 15 Drawing Sheets

(51) Int. Cl.
  *A61B 34/00* (2016.01)
  *A61B 90/00* (2016.01)
(58) Field of Classification Search
  USPC .......................................................... 601/2
  See application file for complete search history.

(56) References Cited

U.S. PATENT DOCUMENTS

| | | | |
|---|---|---|---|
| 2006/0004291 A1 | 1/2006 | Heimdal | |
| 2007/0167806 A1 | 7/2007 | Wood et al. | |
| 2007/0255139 A1* | 11/2007 | Deschinger et al. | 600/443 |
| 2009/0326372 A1 | 12/2009 | Darlington et al. | |
| 2010/0241005 A1* | 9/2010 | Darlington et al. | 600/459 |
| 2011/0060222 A1 | 3/2011 | Thittai | |

OTHER PUBLICATIONS

International Search Report and Written Opinion filed Jul. 16, 2013, in International Application No. PCT/US2013/050767 dated Oct. 25, 2013, 13 pages.

\* cited by examiner

HUMAN INTERFACE AND DEVICE FOR ULTRASOUND GUIDED TREATMENT

CROSS-REFERENCES TO RELATED APPLICATIONS

This application claims the benefit of U.S. Provisional Patent Application No. 61/672,213, filed Jul. 16, 2012, and U.S. Provisional Patent Application No. 61/798,831, filed Mar. 15, 2013, the disclosures of which are incorporated by reference herein in their entirety.

BACKGROUND

The use of focused ultrasound for treating tissues is a relatively new field. Devices providing ultrasound therapy are being developed and new ways are being found for users to interact with such devices.

There is increasing interest in devices that provide image-guided focused ultrasound therapy. With an image-guided ultrasound device, the general principle is to provide the user sufficient information so they can safely and effectively target and treat tissues. Various devices described herein for illustrative purposes use ultrasound imaging for visualization and high-intensity focused ultrasound for treatment.

SUMMARY

The following summary is provided to introduce a selection of concepts in a simplified form that are further described below in the Detailed Description. This summary is not intended to identify key features of the claimed subject matter, nor is it intended to be used as an aid in determining the scope of the claimed subject matter.

This disclosure describes unique ways in which a user may interact with an ultrasound device. It also describes ways in which the device may automatically respond or behave as an alternative to the user interaction.

High intensity focused ultrasound (HIFU) systems described herein provide real-time, image-guided HIFU treatment of tissue. In at least one embodiment, a system includes a HIFU applicator configured to deliver HIFU energy to the tissue, a HIFU generator configured to control and transmit the HIFU energy to the HIFU applicator, an ultrasound imaging device configured to control imaging of the tissue, and a user interface including a display, which may be a touchscreen display. The user interface is configured to display images of the tissue on the display for three-dimensional visualization of the tissue, wherein the images include an active parallel frame depicting a real-time image plane parallel to a feature of the applicator and an active orthogonal frame depicting a real-time image plane orthogonal to the active parallel plane.

The user interface may be further configured to display reference frames in addition to the active parallel frame and the active orthogonal frame, wherein the reference frames include a reference parallel frame and a reference orthogonal frame. In at least one embodiment, the reference parallel frame provides a static view of the active parallel frame and the reference orthogonal frame provides a static view of the active orthogonal frame.

The user interface may be further configured to display reference lines added to the reference parallel frame and the reference orthogonal frame, and duplicate the reference lines on the active parallel frame and the active orthogonal frame. The user interface may include device controls, which may be one or more control icons accessible via the display, for controlling the ultrasound imaging device. In at least one embodiment, the system is configured to automatically set and adjust one or more of the device controls.

The system may be further configured to detect and mark tissue boundaries, calculate and adjust treatment parameters based on the detected tissue boundaries, and display the marked tissue boundaries on the display. The user interface may be configured to display 360-degree sweep view of the tissue volume. The ultrasound imaging device may be connected to the system via a docking interface.

Methods of interacting with a high intensity focused ultrasound (HIFU) system during real-time, image-guided HIFU treatment of tissue are also described herein. In at least one embodiment, a method includes delivering HIFU energy to provide treatment to the tissue, and displaying ultrasound images of the tissue on a user interface during treatment. The images include an active parallel frame depicting a real-time image plane parallel to a feature of the applicator and an active orthogonal frame depicting a real-time image plane orthogonal to the active parallel plane.

The method may further include displaying reference frames in addition to the active parallel frame and the active orthogonal frame during treatment, wherein the reference frames include a reference parallel frame and a reference orthogonal frame. In at least one embodiment, the reference parallel frame provides a static view of the active parallel frame and the reference orthogonal frame provides a static view of the active orthogonal frame.

The method may further include adding reference lines to the reference parallel frame and the reference orthogonal frame, and duplicating the reference lines on the active parallel and active orthogonal frames.

The method may further include controlling an ultrasound imaging device through device controls, which may be one or more control icons accessible on a display. In at least one embodiment, the method includes automatically setting and adjusting one or more of the device controls.

The method may further include detecting, marking, and displaying tissue boundaries, as well as calculating and adjusting treatment parameters based on the detected tissue boundaries. In at least one embodiment, the method includes automatically detecting, marking, and displaying tissue boundaries, and automatically calculating and adjusting treatment parameters based on the detected tissue boundaries. The method may further include displaying a 360-degree sweep view of the tissue volume.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

This section describes various embodiments of therapeutic ultrasound devices that include user interfaces in accordance with the present disclosure.

Figure 1:
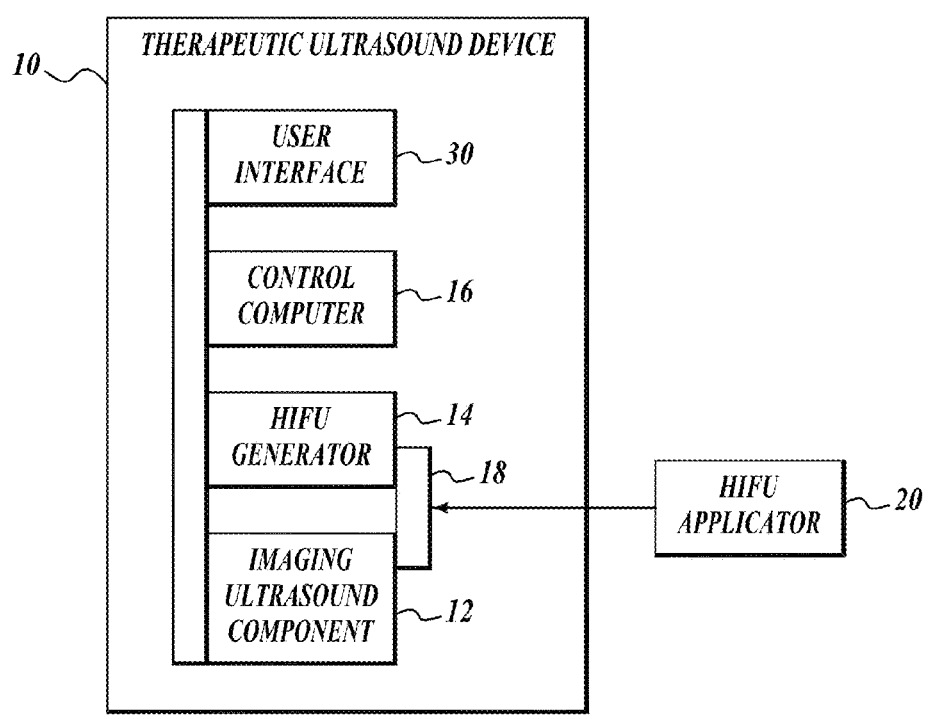
FIG. 1 illustrates a therapeutic ultrasound device in accordance with at least one embodiment.

The primary components of at least one embodiment of a device described herein (see FIG. 1) are listed in Table 1.

TABLE 1

Device primary components

| Number | Description |
|---|---|
| 10 | HIFU device |
| 12 | Ultrasound imaging component (preferably, commercial grade) |
| 14 | HIFU generator that controls and outputs the power waveform to the HIFU transducer |
| 30 | User interface that includes a video/image display with touchscreen for input, and a footswitch |
| 16 | Computer for interfacing the primary device components |
| 18 | Connector and associated cabling to interconnect the HIFU generator and imaging components to the HIFU applicator |
| 20 | HIFU applicator that houses the HIFU transducer, imaging transducer, high bandwidth ultrasound receiver, and motors/mechanisms for steering the HIFU energy |

Figure 2:
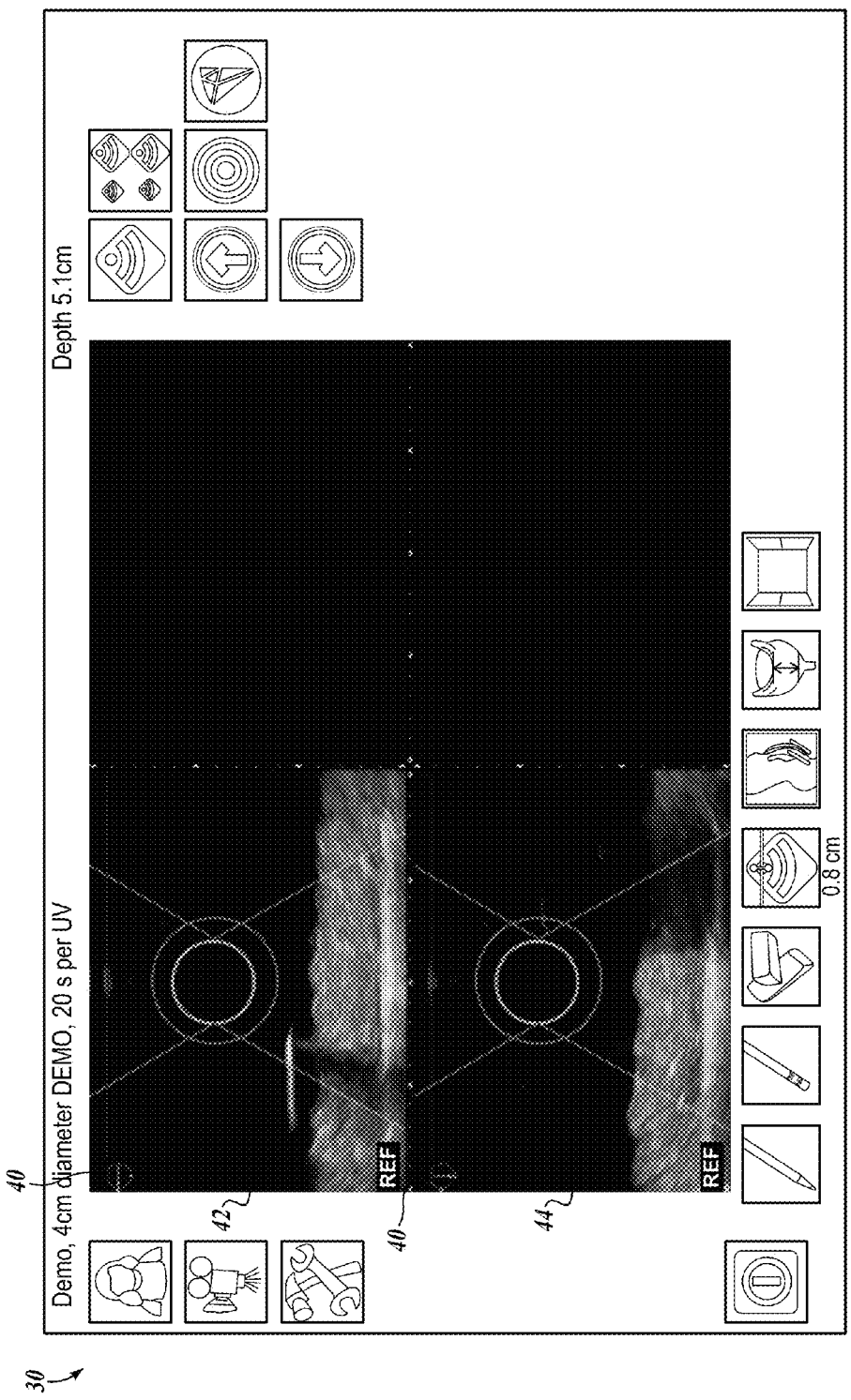
FIG. 2 illustrates a user interface layout including an initial screen with two orthogonal image planes depicted in accordance with at least one embodiment.

In at least one embodiment, an image-guided focused ultrasound device 10 includes a user interface 30 that gives a user the ability to visualize patient tissues in real time both while targeting and treating the tissues. In at least one embodiment, the user interface 30 provides the user with images for visualizing three-dimensional tissue volumes. The user is provided with two real-time orthogonal views 42, 44 (e.g., x-z and y-z planes, or from the user's perspective in this particular embodiment, transverse and sagittal planes), preferably simultaneously, to allow basic three-dimensional visualization of the patient's tissue and tracking of ultrasound therapy applied to the tissue (see FIG. 2). An active parallel frame 42 provides the real-time view of the sagittal image. When appropriately positioning the applicator, the parallel plane passes through the long axis of the applicator and is parallel to a line passing through a feature of the applicator, such as both handles (this plane is typically parallel to the user). An active orthogonal frame 44 provides the real-time view of the transverse plane, which is orthogonal to the active parallel frame 42, as shown in FIG. 2.

The user interface 30, as described herein, may include a variety of icons that allow the user to select certain functionality and otherwise interact with the ultrasound device 10. In the embodiment shown in FIG. 2, for example, an icon 40 is shown in the upper left corner of each image 42, 44 to indicate the orientation (position) of the respective image plane within the patient's tissue. To correlate the image plane to the patient, a corresponding indication on the ultrasound applicator 20 may be provided in the form of a color, shape, or other markings or features. The implementation described herein is intuitive. For an applicator 20 with two handles spaced at 180 degrees apart, one image aligns with the user's hands (handles), and the other image aligns orthogonal to a plane through the user's hands. The corresponding applicator motion is also intuitive as well, since a left motion along the plane through the handles may result in the tissue "sliding" through the ultrasound image (as if one were looking though a scope or view finder). The orthogonal plane can be programmable or selectable as to whether pushing the applicator 20 away results in a "left slide" or a "right slide" of the applicator 20 over the tissue. In addition, there is a provision for displaying a graphic of the applicator 20 moving over the patient on the screen of the user interface 30. The device 10 may use accelerometer data from the applicator 20 (or other input information, such as image data) to determine the motion of the applicator 20 and reflect that motion on the screen of the user interface 30. The orientation of the patient relative to the applicator 20 is settable by the user (e.g., head to the left or right). This mode would primarily be available in a training mode, but could be available during treatment. This data would also be available for motion detection during treatment, could be used independently or combined with processed ultrasound image data to detect motion, and may inform or alarm the user during treatment (e.g., regarding a shift during treatment).

Figure 3:
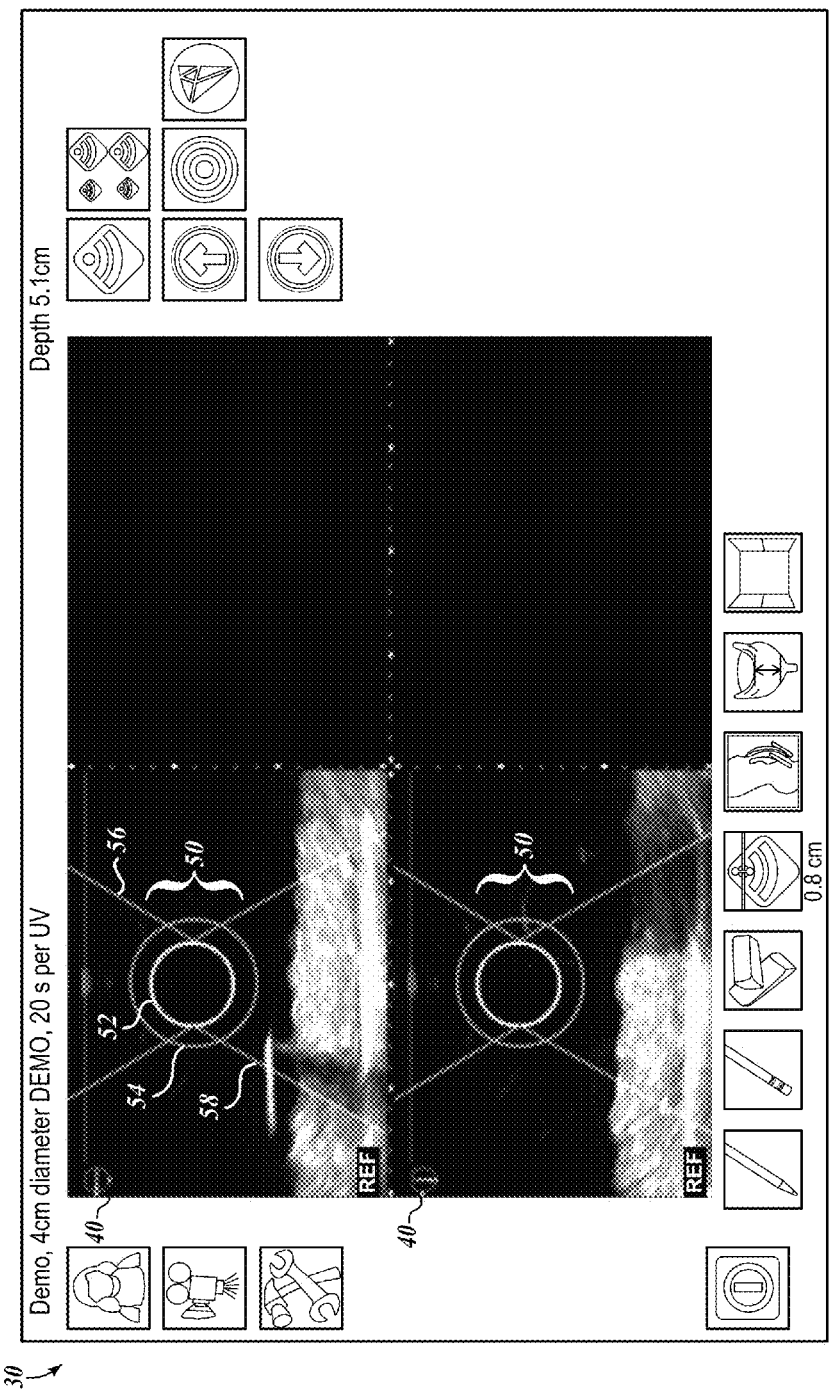
FIG. 3 illustrates a user interface layout including a screen with a graphical overlay of the embodiment illustrated in FIG. 2.

With regard to identifying target tissue, a graphical overlay 50 on the screen of the user interface 30 may be used to show the target volume 52, a safety margin 54, and pre focal and post focal field lines 56, 58 (see FIG. 3). The target volume 52 indicates the tissue to be treated. The safety margin lines 54 indicate the distance away from the target volume 52 to keep critical tissue away such as the serosa, bowel, etc. The pre focal and post focal lines 56, 58 indicate the boundaries of the overall HIFU field for the entire treatment (e.g., as the focus is moved about). The overlay 50 can be turned off or disabled with overlay on/off icon 92 for unobstructed viewing, then re-enabled when desired, e.g., for treatment (see FIG. 7).

In addition, the device 10 may provide the user with a full-volume scanning mode (see icon 100 of FIG. 7), where the scanplane is rotated about a vertical axis, e.g., a full 180 degrees, to allow the user to visualize some portion or an entire volume of tissue. The relative angle of rotation is either automated or manually positioned via the user interface 30 (see FIG. 4).

Figure 4:
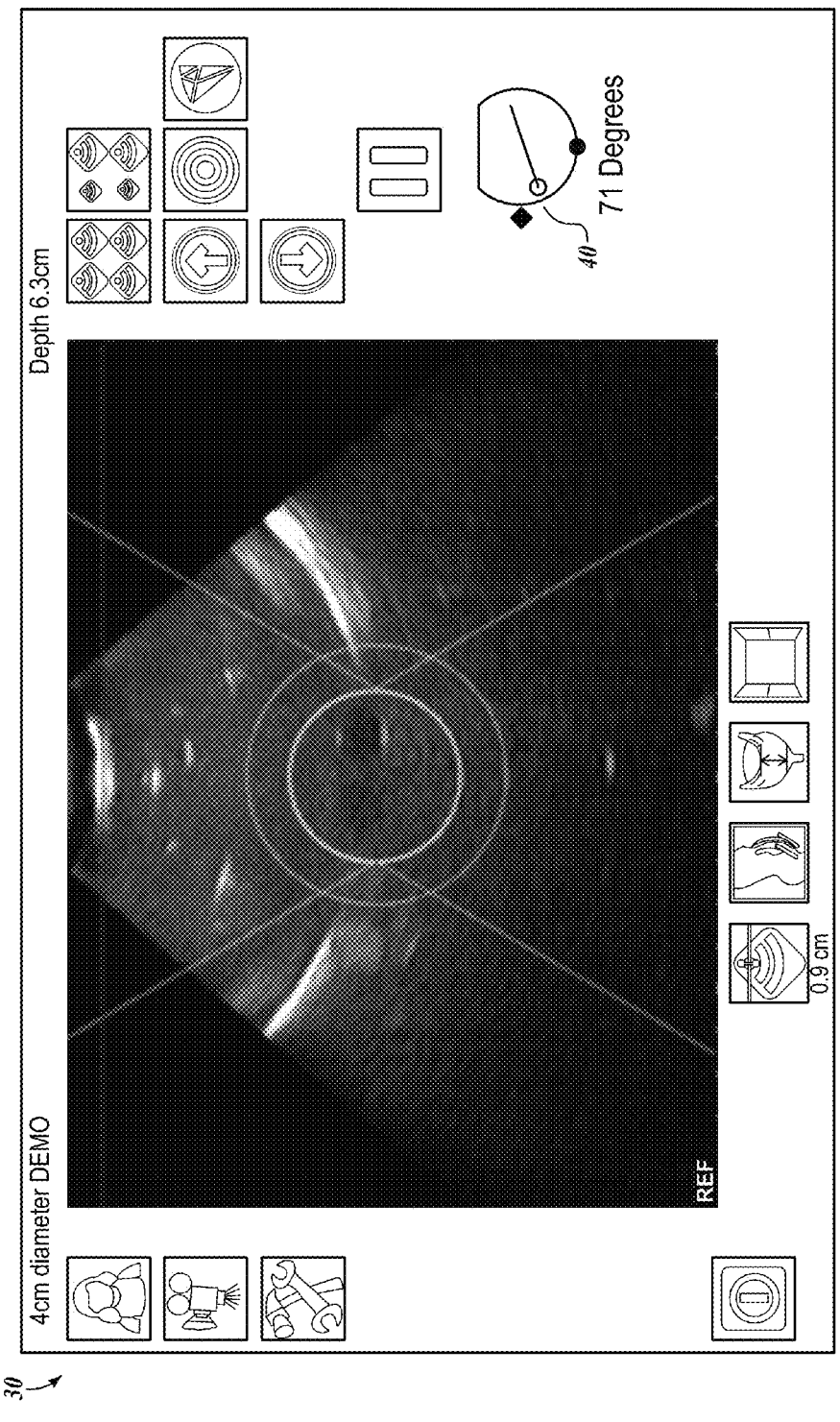
FIG. 4 illustrates a user interface layout including a screen with a layout with a full volume mode.
Figure 5:
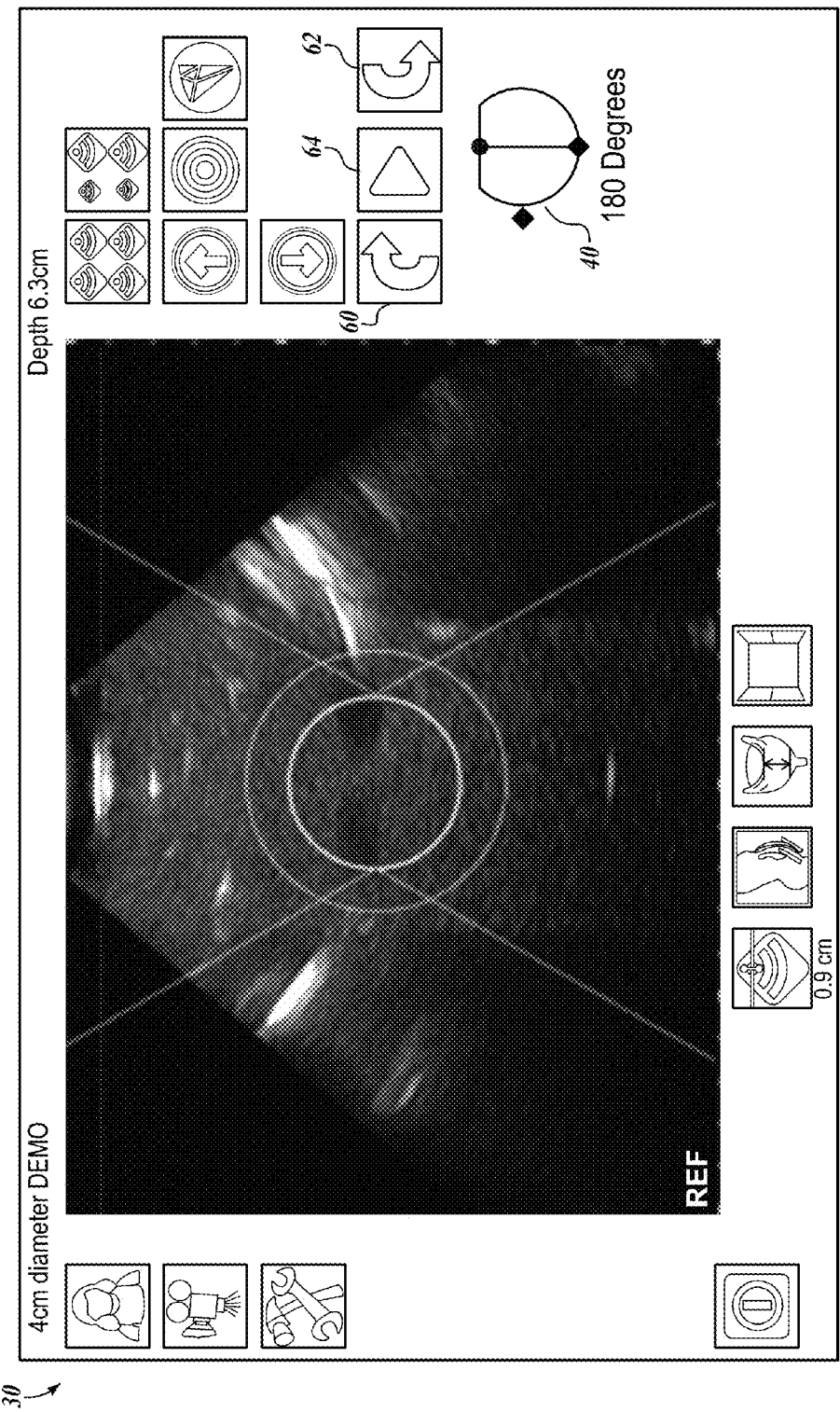
FIG. 5 illustrates a user interface layout including a screen with a scanplane position manual control.

The scanplane position (angle) of the ultrasound image, specifically relative to the applicator and indirectly relative to the patient, may be indicated to the user via the same icon 40 used to reference the orientation of the aforementioned orthogonal scanplanes (see FIG. 4). In addition, the user may pause the automatic sweeping of the scanplane position and manually position the scanplane using controls 60, 62, 64, for example, as shown in FIG. 5.

In at least one embodiment, the user can rotate the image plane in either a clockwise or counterclockwise direction by momentarily, repeatedly, or continuously selecting the respective step icons 62, 63. To restart the automated sweeping, the user selects the Sweep/Pause icon 64.

Upon exiting the targeting mode, the user is provided two targeting image frames. Reference parallel frame 46 and reference orthogonal frame 48 are maintained for reference (left), and two additional image frames (right) become active, namely active parallel frame 42 and active orthogonal frame 44 (see FIG. 6). In the active parallel and orthogonal frames 42, 44, the tissue can be observed in real time, while in the reference parallel and orthogonal frames 46, 48, the image of the tissue is captured at one point in time, for example.

The right-side active image planes (active parallel frame 42 and active orthogonal frame 44) are used for real-time tracking of tissue treatment throughout the treatment session, with the reference image planes (reference parallel frame 46 and reference orthogonal frame 48) remaining constant on the left side. Also shown on the screen of the user interface 30 is an icon 70 used for selecting between various image filters. These image filters include, but are not limited to, filters that remove image reverb artifacts using various techniques and/or edge, boundary, or tissue-enhancing filters. In the illustrated embodiment, most controls are available in both the targeting and pretreatment modes (see FIG. 7).

The user can modify treatment parameters, initiate treatment, or exit/power off. The characteristics of these controls and other interactions or features of the device 10 will be discussed below.

Figure 6:
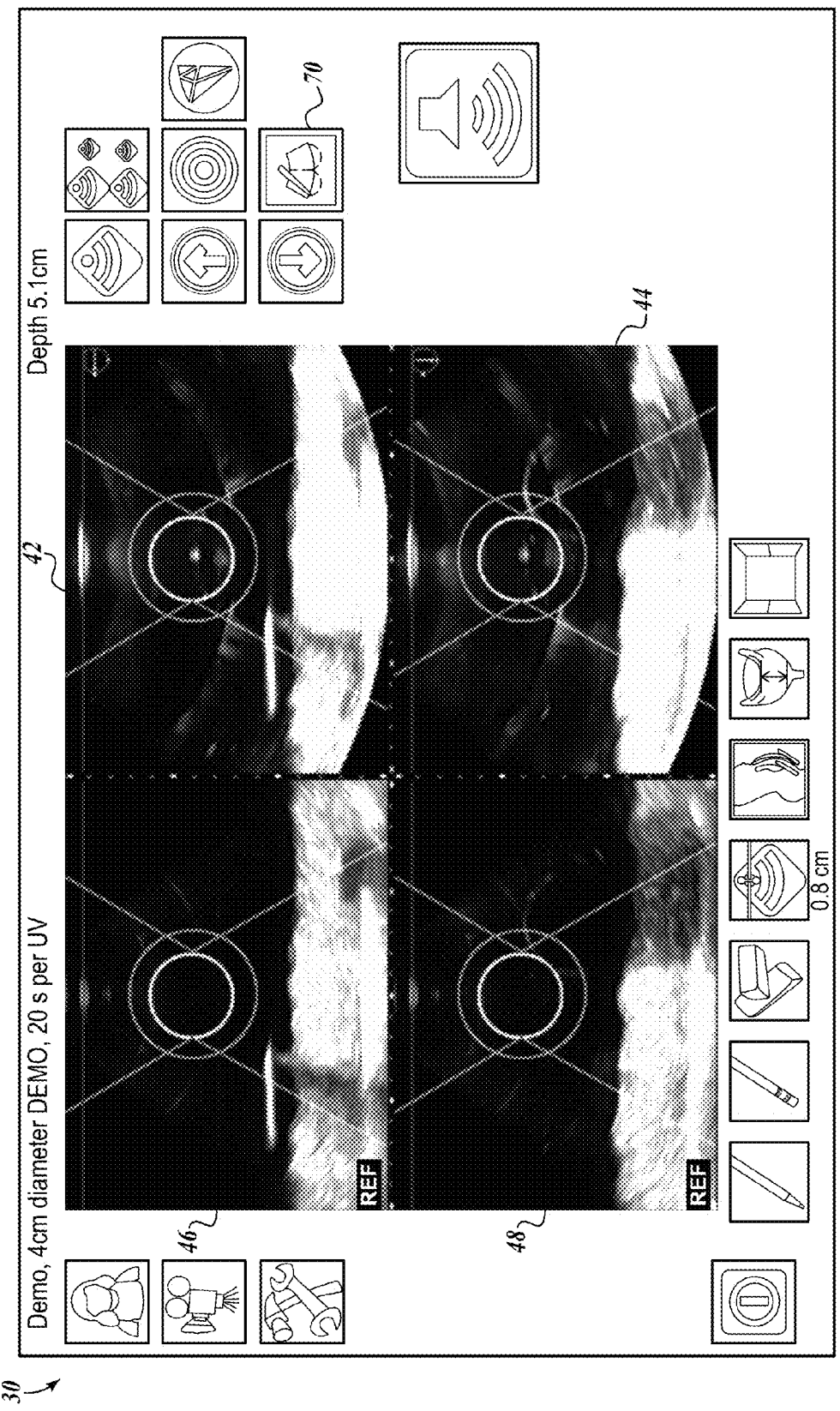
FIG. 6 illustrates a user interface layout including a pretreatment screen showing reference and active images.

The device 10 may incorporate multiple features that assist the user in tracking the patient's tissue during treatment. First, the reference planes (reference parallel frame 46 and reference orthogonal frame 48) on the left side of the screen of the user interface 30, which show the targeted tissue, stay consistent throughout treatment (FIG. 6). The intent is to keep the applicator 20 positioned such that the active images (active parallel frame 42 and active orthogonal frame 44) on the right side of the screen of the user interface 30 consistently appear like the reference images. The reference planes are used to ensure that the position of the applicator 20 relative to the patient remains consistent during treatment. In addition, in cases where the user moves the applicator 20 in an unintended direction, the patient moves, or the applicator 20 is otherwise not on target, the user can pause the treatment, reposition the applicator 20 such that the active images are aligned similar to the reference images, and then restart treatment.

Figure 7:
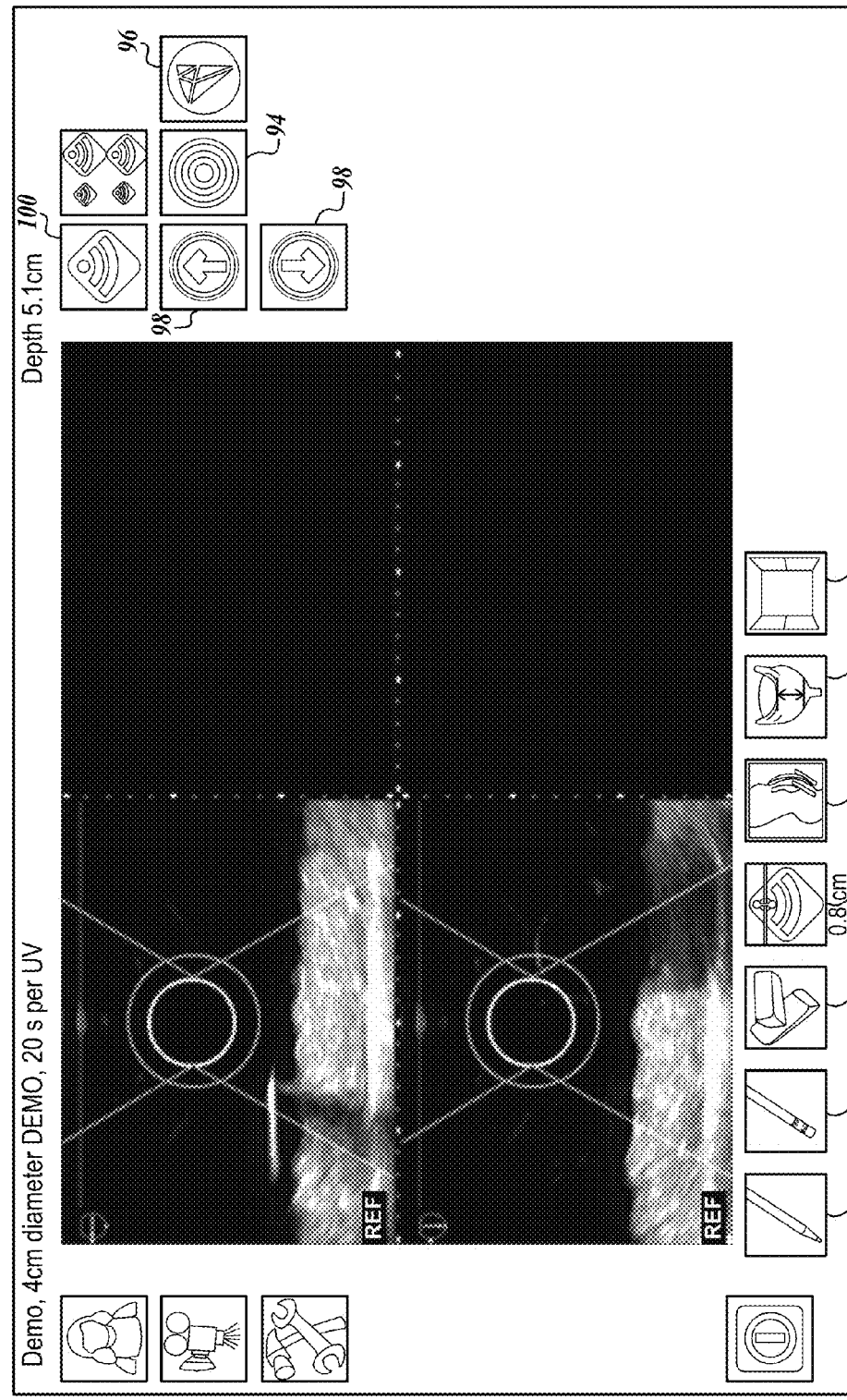
FIG. 7 illustrates a user interface layout including a screen with user controls in a targeting mode.
Figure 8:
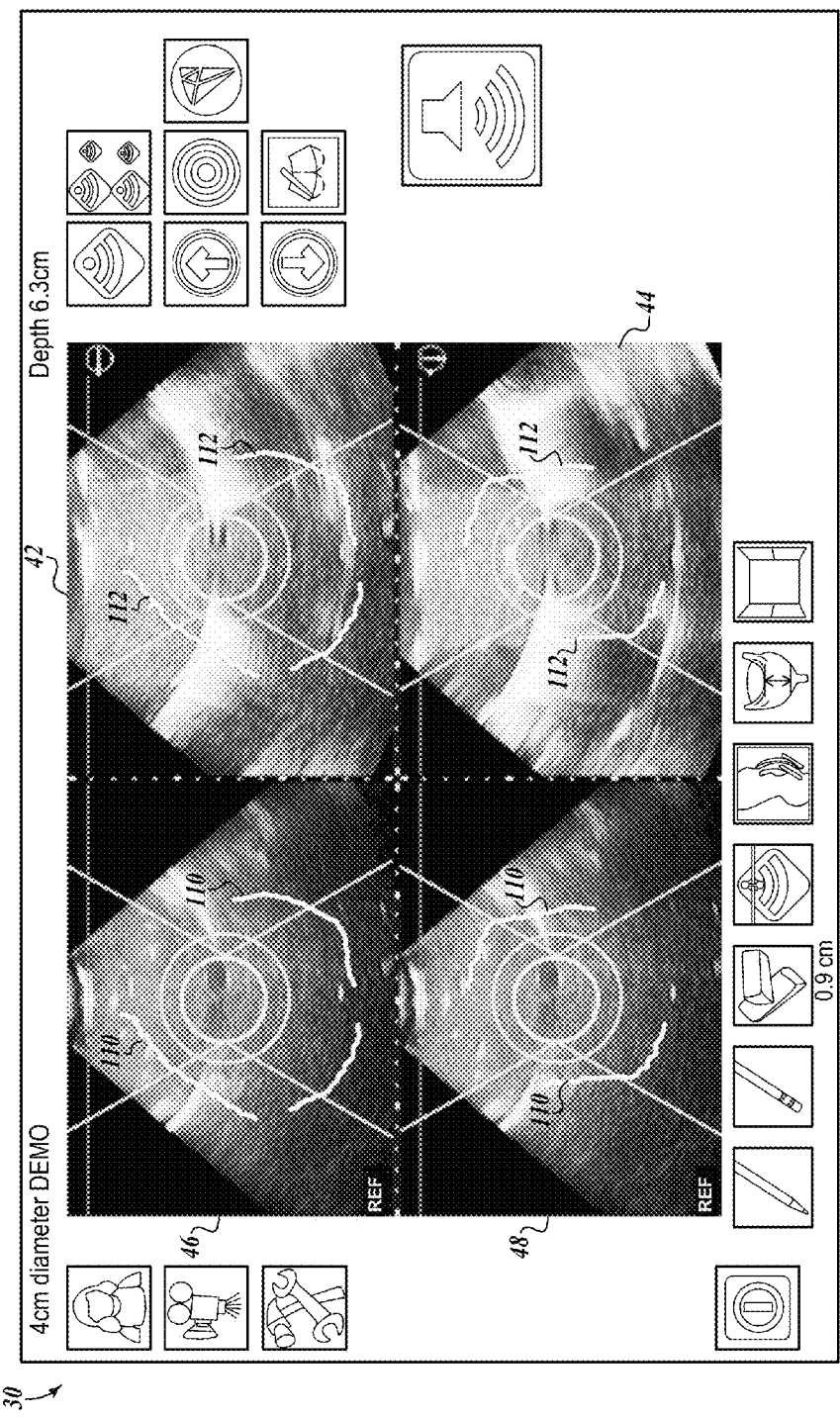
FIG. 8 illustrates a user interface layout including a screen displaying sketched reference lines.

Second, the user has tools 80, 82, 84 for drawing or sketching reference lines 110 on the reference plane images (see FIGS. 7 and 8). These reference lines 110 are typically used to mark tissue boundaries. The reference lines 110 can be drawn with finger, stylus, mouse, trackball, touchpad, or other suitable device on the touchscreen display of the user interface 30. These reference lines 110 are thereafter duplicated 112 on the active plane images, which assist the user in keeping the applicator 20 on target (FIG. 8). In addition to the drawing tool 80, there is an eraser tool 82 for erasing part or all of a reference line, and an erase function 84 for erasing all reference lines. The eraser tool data may be input via finger, stylus, and/or other tools similar to the line-drawing tool. As with the overlay 50, the lines 110, 112 can be visible or hidden for unobstructed viewing of the ultrasound image.

Reference lines 110 could also be generated automatically using common signal and image-processing techniques that can detect dominant features, such as boundaries or edges, in the reference images. Upon activation by the user (or automatically), the device 10 may present the user with proposed reference lines based on detected features, from which the user can choose to accept all, some, or none as reference lines on the screen of the user interface 30. In addition, an embodiment of the device 10 may enhance the tissue boundaries (edges) using currently known signal and image-processing techniques (e.g., enhancing steep gradients across the image data).

Figure 9:
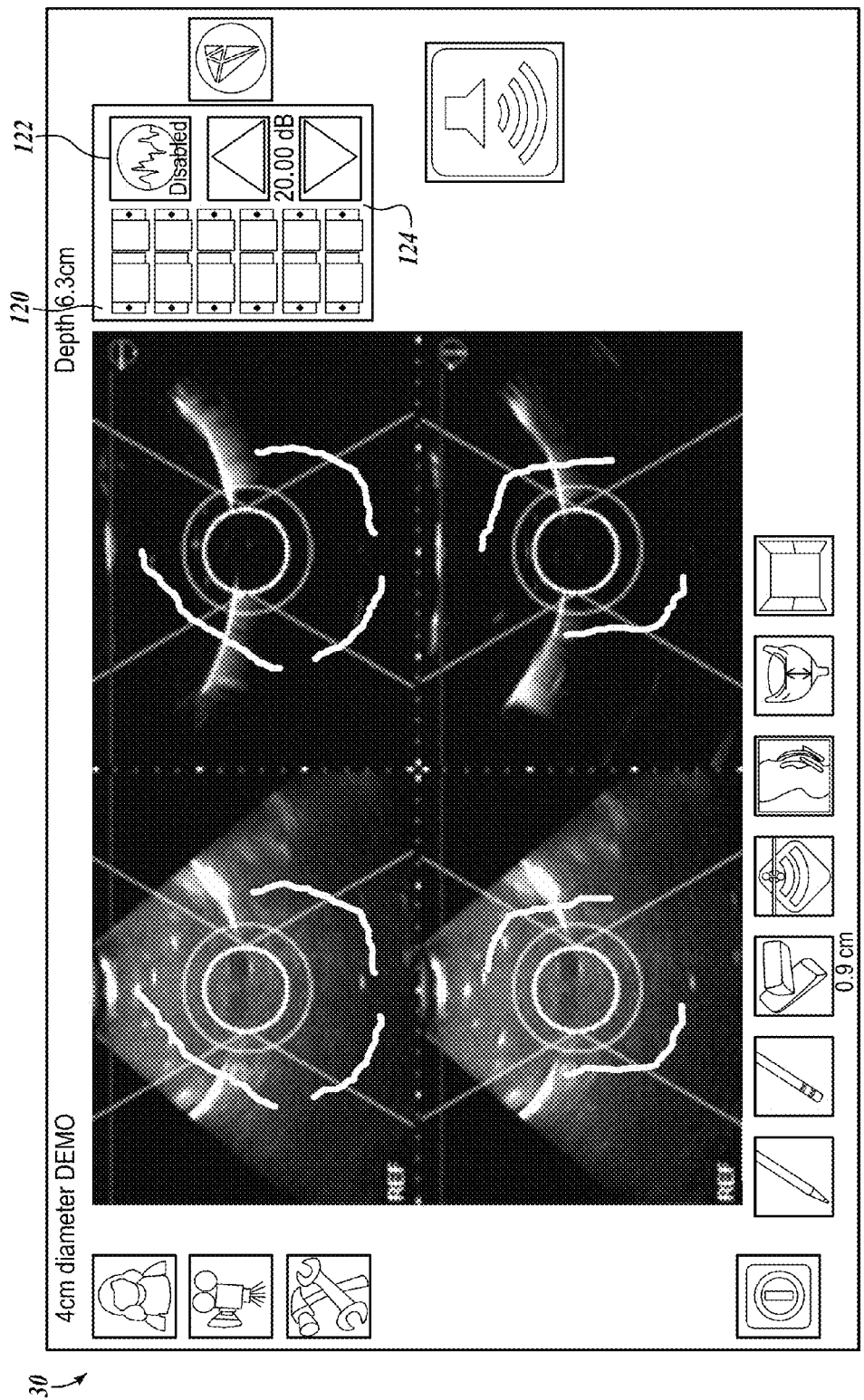
FIG. 9 illustrates a user interface layout including a screen with an ultrasound imager control panel.

The device 10 may incorporate an ultrasound imaging system for visualizing the patient's tissues. The ultrasound imaging system may be a commercially available system. As described herein, controls for a commercial ultrasound system may be included in the user interface 30 of the HIFU device 10 (see FIG. 9) by activating icon 96 (see FIG. 7).

In the illustrated embodiment, the ultrasound imaging controls presented to the user include Time Gain Control (TGC) 120, enabling or disabling harmonic imaging 122, and adjusting the overall gain 124. In other embodiments, the user interface 30 may be further enhanced with additional or different imaging ultrasound controls that are presented to the user. In addition to the user controls, there are controls that may be automatically adjusted by the device 10, such as overall gain and TGC presets, and automatic gain change as depth is varied.

In at least one embodiment, the distance between the imaging transducer and the patient interface varies as a function of the HIFU treatment depth, since the imaging transducer is moved along with the HIFU transducer within a transducer fluid volume. The transducer fluid path increases and the tissue path decreases as the depth of treatment decreases. In this embodiment, the device 10 reduces overall gain of the ultrasound imaging system to account for the reduced tissue path between the transducer and the target volume. For some imaging systems, the device 10 can also adjust the output power as the transducer fluid path length is varied.

In addition, the device 10 may provide the user with options for edge-enhancing filters (e.g., enhancing steep gradients in the image), reverb and motion filtering (via Doppler and/or minimum filtering), elastography methods to enhance differences in tissue stiffness, and other ultrasound imaging enhancements that assist the user with differentiating between tissue types (e.g., clearer identification of fibroid boundaries).

The device 10 may include multiple features by which the user can set or adjust the treatment regimen for affecting treatment parameters. For example, in at least one embodiment, the user first operates the device 10 to choose a target volume. The device 10 may provide an icon on the user interface 30 that, when selected, brings up a menu of treatment volume options (using, for example, a scrolling, mouse, or touch screen selection). Alternatively, the target volume shown on the screen of the user interface 30 could change size or shape each time the user selects the icon 94 on the screen of the user interface 30 (see FIG. 7). The icon 94 could also change (e.g., by way of text or graphic) with each target volume selection, providing feedback to the user. Alternatively, in other embodiments, the device 10 iteration(s) may allow the user to change the size of the volume simply by touching or clicking on the target volume boundary on the user interface 30 and dragging the boundary to the desired target volume size and/or shape.

Every target volume may have associated with it a unique set of treatment parameters, such as peak acoustic power, duty cycle, and motion pattern. In at least one embodiment, an overall target volume is made up of multiple unit volumes and the treatment parameter(s) set for each unit volume is/are dependent on where the unit is located relative to the other unit volume(s). In an embodiment, the device 10 is implemented using predetermined treatment volumes (e.g., spherical shapes), though other embodiments may include an interface that allows the user to sketch arbitrary shapes on the orthogonal planes (or more than two planes), if desired. In such embodiments, the device 10 is configured to interpolate between the sketched lines and create a volume based on the sketched boundaries. The created target volume is displayed for the user to modify or accept. The device 10 then uses one or more algorithms to determine the appropriate treatment parameters for treating the target volume as displayed.

Second, the treatment regimen may be affected by the depth of treatment, due to the attenuation of the ultrasound as it passes through the tissue. In at least one embodiment of the device 10, the user chooses a target depth for the tissue volume via arrows 98 on the screen of the user interface 30 (see FIG. 7). The arrows 98 could be replaced with similar functions such as a slide bar or entered numeric value. Further device 10 enhancements may include the ability to touch or click on the target volume and drag the volume to a new target depth on the touchscreen of the user interface 30.

Third, the treatment regimen may be dependent on the presence of other physiological aspects of the patient, such as bladder fluid, in the acoustic path. In at least one embodiment, the device 10 provides cursors on the screen of the user interface 30 to mark upper and lower boundaries of the bladder. In cases where bladder fluid is in the acoustic path, the user may select one or more icons 90 on the screen of the user interface 30 to make the cursors visible and then mark the bladder upper and lower boundaries. The user may adjust the cursor positions by dragging them via the touch screen of the user interface 30, though one could use a stylus, mouse, arrow keys, entered value, or other means to adjust the positions.

In one embodiment, the user is presented with simple line cursors. In other embodiments, the user interface 30 is enhanced to include curved or arbitrary lines for more complex and more precise calculation of the treatment parameters. In addition, embodiments of the ultrasound device 10 may automatically detect the boundaries of the bladder using known boundary detection algorithms on the image data, and use subsequent calculations to determine the treatment parameters based on the detected boundaries, thus eliminating the need for the user to interact with this parameter.

Fourth, the treatment parameters may be influenced by the thickness of the patient's abdominal wall. Similar to the bladder, in at least one embodiment, the user can enable a cursor on the screen of the user interface 30 and use the cursor to identify the abdominal wall depth as well as adjust the position of the cursor to mark the lower wall boundary. Methods of adjusting the cursor utilize icon 88 and are similar to the aforementioned methods for adjusting the bladder wall cursors (see FIG. 7). In addition, similar to the bladder wall detection, embodiments of the device 10 may use currently known (or future developed) methods to automatically determine the abdominal wall boundary and subsequently calculate and adjust the treatment parameters. In both cases, the automatically determined boundaries could be presented to the user (e.g., via the screen of the user interface 30) for verification and/or modification.

Fifth, in embodiments of the ultrasound device 10 where the patient interface cap is flexible and the transducer fluid path length between the transducer and the patient tissue is dependent on the volume of transducer fluid in the system, the device 10 may be configured to account for the fluid standoff in the process of calculating the output power of the ultrasound signals. The position of the patient interface relative to the transducer may be adjusted by the user (e.g., using the screen of the user interface 30) or may be automatically determined by the device 10. In the embodiment illustrated above, the "skinline marker" icon 86 (see FIG. 7) activates a blue line marker (cursor) on the image that is used to mark the surface of the patient's tissue (skin). This manual feature is implemented and used in at least one embodiment of the device 10, though the feature may be automated in other embodiments of the device 10. In an automated embodiment, the device 10 processes the image data to identify the boundary of the patient's tissue by looking for the transition from the foreground dark or low amplitude reflection data to the first bright or high amplitude reflection data. Other processing techniques may be used to detect this transition, such as processing raw RF data for the first significant reflection. This first transition is the patient's skin, which is then used for calculating the standoff distance.

Figure 10:
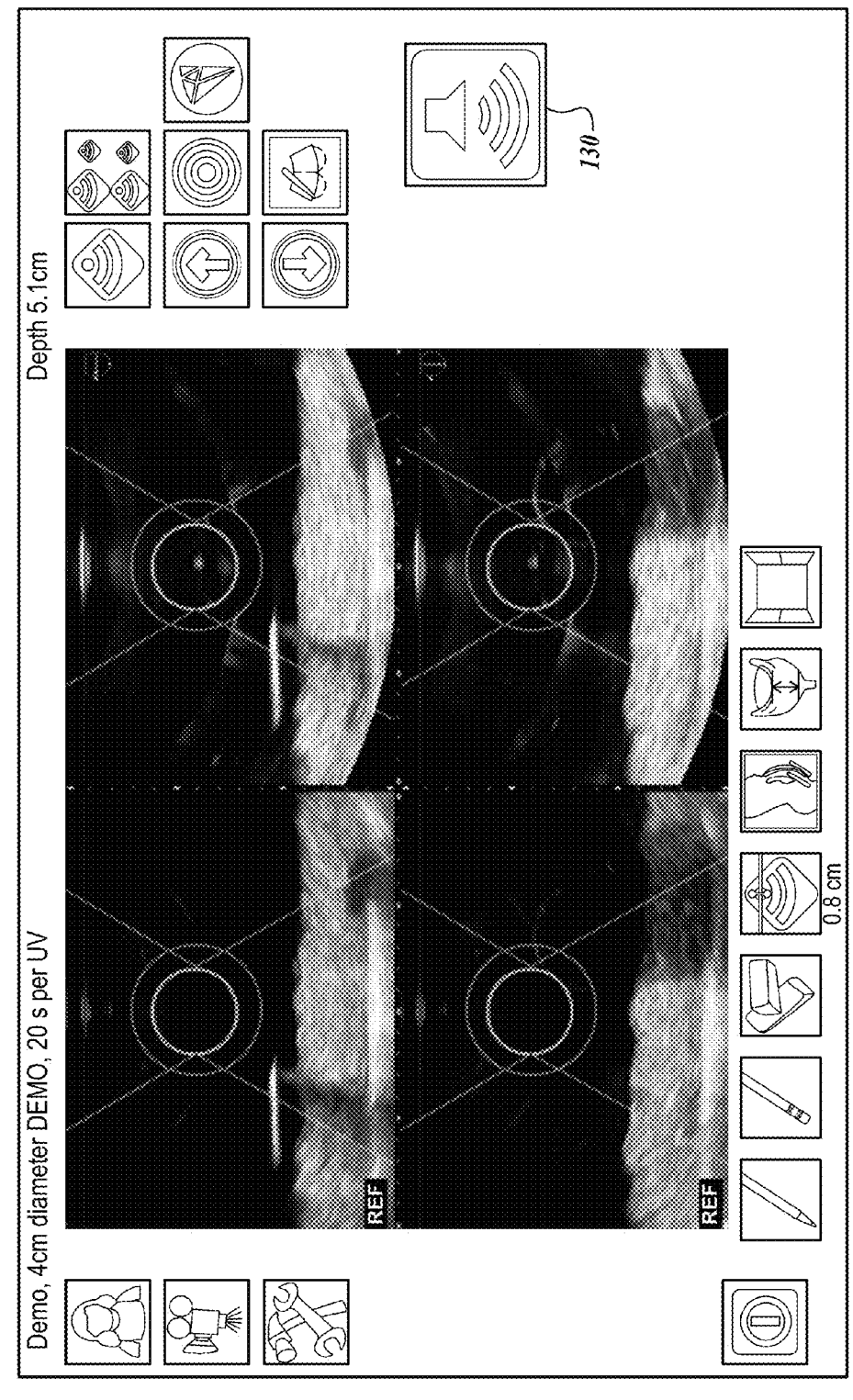
FIG. 10 illustrates a user interface layout including a pretreatment screen with a footswitch control.

When in pretreatment mode, the user is presented with the option of enabling the footswitch (see FIG. 10), in at least one embodiment. Upon activation of the footswitch, the Activate Footswitch icon 130 may be configured to change to an Activate Treatment icon, and the device 10 programs the HIFU parameters and positions the transducer to start treatment. The device 10 is in Treatment Mode while the footswitch is enabled and the device 10 is either ready to treat or actively outputting HIFU signals.

When the user presses the footswitch, the icon changes from the Activate Treatment icon to a Stop/Pause Treatment icon, and the device 10 implements a regimen to treat the targeted treatment volume. The device 10 disables the footswitch and notifies the user when treatment is complete, at which time the icon changes back to indicate a pretreatment state. If the user releases the footswitch before the device 10 completes treatment, the icon may be configured to change to an inactive Treatment Paused icon, and the device 10 enters a Treatment Paused state.

In the Treatment Paused state, the device 10 may be configured to display options to the user. The user may choose to cancel the treatment and return to the pretreatment state, or simply re-press the footswitch to continue treating the target volume using the previously determined treatment regimen. While in the Treatment Paused state, the user may also choose to enter an imaging state and conduct a full volume sweep of the target volume to verify the conditions of the target volume and acoustic path, return to the Treatment Paused state, and then choose to cancel or return to providing treatment to the patient's tissue.

While outputting therapeutic ultrasound signals, the device 10 may include multiple indicators to the user that treatment is active. The device 10 may emit a sound, show an icon on the screen of the user interface 30 (e.g., the treatment icon changes to a stop treatment icon, and/or other indications), and/or illuminate the applicator 20 while outputting treatment. In addition, there may be a treatment timer on the screen of the user interface 30 indicating progress of the treatment regimen to the user. This treatment progress indicator could also be implemented with a progress bar, shading the target volume, or other relevant means of indication.

Although the embodiments of the device 10 discussed above are implemented with a footswitch, other embodiments of the device 10 could incorporate one or more control switches on the applicator 20, voice commands, proximity sensors, combinations of the aforementioned, or other means for the user to activate the output of HIFU signals.

While outputting treatment, an uncoupled applicator 20 (relative to the patient) would not harm the patient, though it would not result in effective treatment and such conditions could potentially harm the applicator 20. In at least one embodiment, the device 10 monitors the HIFU signal reflected from the patient interface and compares it to a predetermined threshold. If the reflected signal is greater than the threshold, the device 10 assumes the applicator 20 is not fully coupled to the patient and notifies the user. A value lower than the threshold would indicate the device 10 is coupled to the patient. In other embodiments, the thresholds and comparisons may be configured differently such that a value lower than the threshold indicates the applicator 20 is not fully coupled, and a value higher than the threshold indicates the device 10 is coupled to the patient. In addition, the device 10 may be configured to monitor the HIFU signal(s) reflected from tissues deeper than skinline (e.g., near focus) and compares these with expected values. This data may be combined with other data to enhance the coupling detection algorithm.

While in some embodiments, the device 10 allows the entry of patient data (e.g., name, etc.) and stores device data during treatment (for analysis, etc.), other embodiments of the device 10 may not provide the user with an option to enter patient data and device 10 does not store data during treatment. Further embodiments of the device 10 may allow the user to input patient data, treatment planning information from past, current, or future treatments, or other related data. In addition, the device 10 could also store treatment data (values, video, and images) from a given treatment session or sessions for later use by the user or others.

Preferably, the device 10 incorporates multiple features that enhance the safety of the device 10. First, embodiments of the device 10 may detect and inform the user in case of insufficient coupling, as discussed above. The energy reflected off the patient interface from the HIFU waveform is monitored, and if it is too high (or too low) of a value, the device 10 may determine that the device 10 is not properly coupled, cease outputting treatment, and inform the user to check the patient coupling.

Further embodiments of the device 10 may include monitoring the tissue boundaries in the active image(s) and comparing them to the position of the tissue boundaries in the reference image(s). If the boundaries are not found to be within a predetermined value (threshold), a warning may be displayed or communicated to the user to check the alignment of the applicator relative to the patient. The user could pause treatment, realign the applicator 20 over the target tissue, or choose to ignore the warning. If the boundaries are not found to be within a second predetermined threshold (value), the device 10 may automatically pause treatment and an error may be displayed or communicated to the user indicating the treatment is paused and to check the alignment. The user would then reposition the applicator 20, clear the error, and reinitiate treatment, thereby continuing to treat the target volume. As a secondary means of ensuring an aligned applicator 20 is on target (where the primary means is the user monitoring the ultrasound images), the user may have the option to set the two thresholds and enable or disable the feature. Additional configurations include an accelerometer that can be used independently or combined with the image data to determine motion of the applicator 20 and accordingly inform the user.

The device 10 includes the ability to use independent ultrasound imaging for general ultrasound imaging. For example, there are two implementations of this feature described below. Table 2 below sets forth various ultrasound imaging components shown in the accompanying figures and described herein.

TABLE 2

| Number | Description |
|---|---|
| | General ultrasound imaging components |
| 10 | Therapeutic ultrasound device |
| 12 | Imaging ultrasound component |
| 22 | Connection between the imaging ultrasound component and the rest of the therapeutic ultrasound device |
| 24 | Hand-held ultrasound imaging probe |
| 26 | Connector between the ultrasound imaging probe and the therapeutic ultrasound device |

Figure 11:
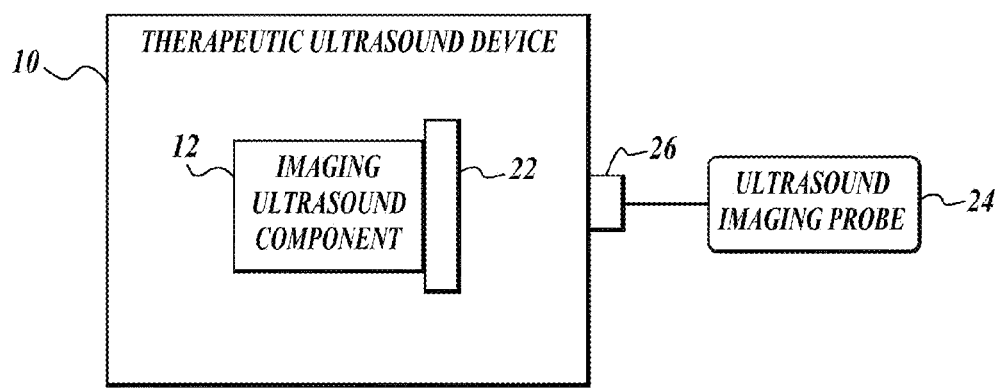
FIG. 11 illustrates a therapeutic ultrasound device in accordance with at least one embodiment.

In at least one configuration of integrated diagnostic imaging ultrasound, the HIFU device 10 incorporates one or more connection(s) 26 for hand-held ultrasound imaging transducer(s) 24 (see FIG. 11). The HIFU device 10 is then used as a diagnostic ultrasound imaging system.

In a dockable portable ultrasound configuration, the ultrasound imaging component 12 is disconnected via a docking interface 22 by the user from the HIFU device 10. The ultrasound imaging component 12 is then connected via connector 26 directly to the imaging transducer 24 and used as a stand-alone diagnostic ultrasound imaging system.

Alternative user interface layouts include multiple screen layouts for alternative user interaction with the device 10. In one embodiment, the screen of the user interface 30 has two active image planes and two reference image planes (see FIG. 12).

In this embodiment, the right-side screens display two orthogonal images (active parallel frame 42 and active orthogonal frame 44) and are always active (imaging). The left-side screens (reference parallel frame 46 and reference orthogonal frame 48) are blank on first entry to the user interface, and are populated with images from the right side when the user chooses (e.g., selects capture image) or when the user selects to start treating (e.g., activates the footswitch). The feature of capturing the images may be selected via a variety of modes, including, but not limited to, a footswitch, switch/sensor on the applicator 20, voice command, or through a touchscreen of the user interface 30. If the user has preselected captured images prior to activating the footswitch, the user may be prompted to choose whether the previously captured images are to be replaced. Once the device 10 is in treatment mode, the reference images (reference parallel frame 46 and reference orthogonal frame 48) are static and do not change. In other embodiments and/or use conditions, the static images, namely reference parallel frame 46 and reference orthogonal frame 48, may be replaced while in treatment mode.

Figure 12:
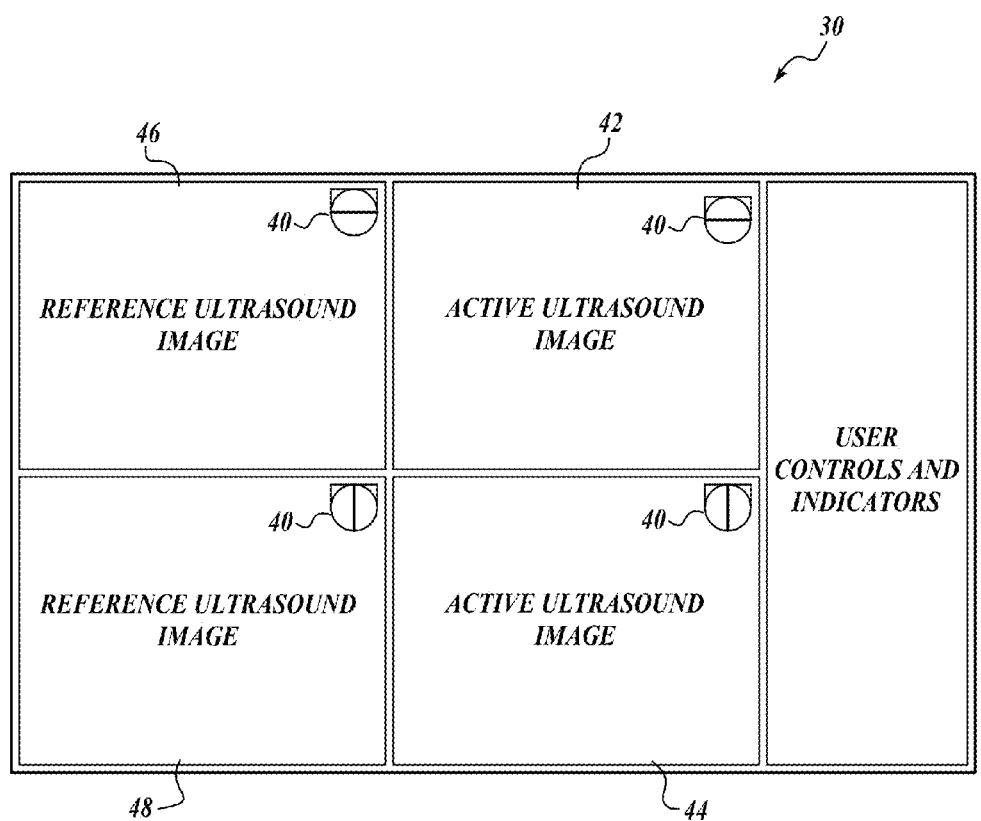
FIG. 12 illustrates a user interface layout including a screen layout with two active image planes and two reference planes.
Figure 13:
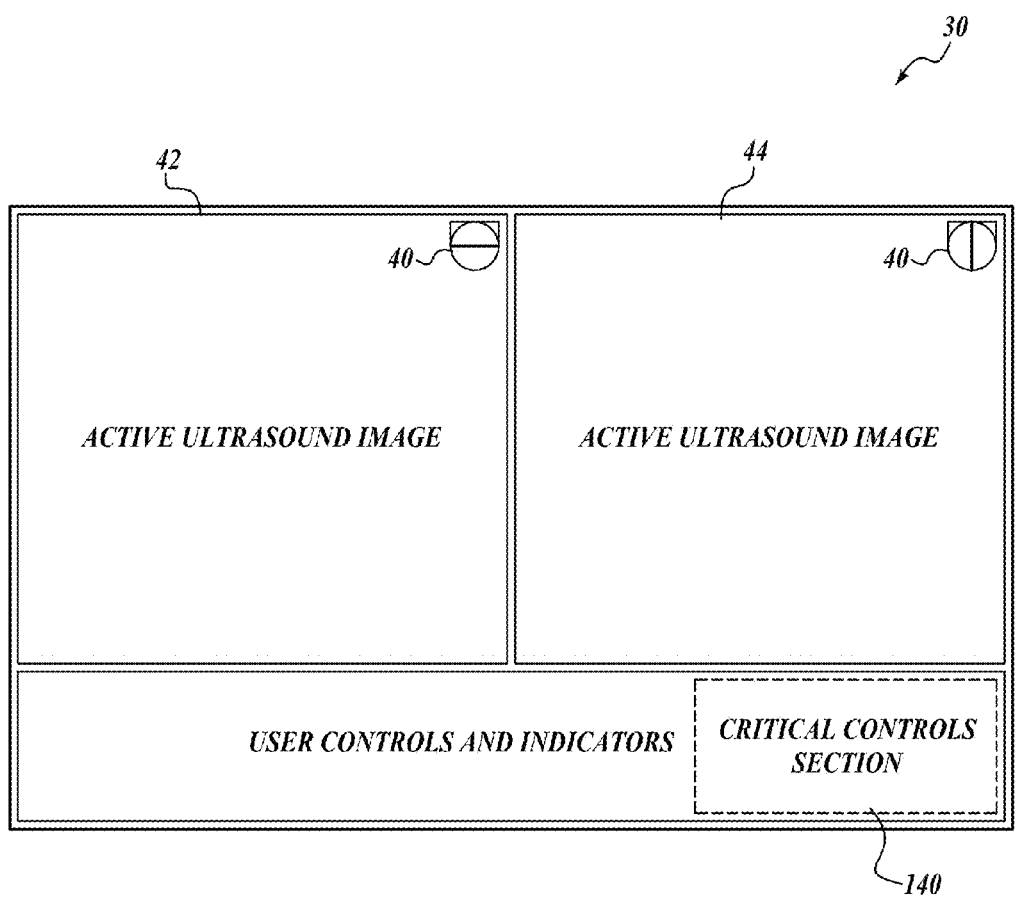
FIG. 13 illustrates a user interface layout including a screen layout with two image planes.

In another embodiment, the screen of the user interface 30 has only two active image planes that are visible, namely active parallel frame 42 and active orthogonal frame 44 (see FIG. 13), and the image planes have a larger format than that with four image planes (see FIG. 12).

Figure 14:
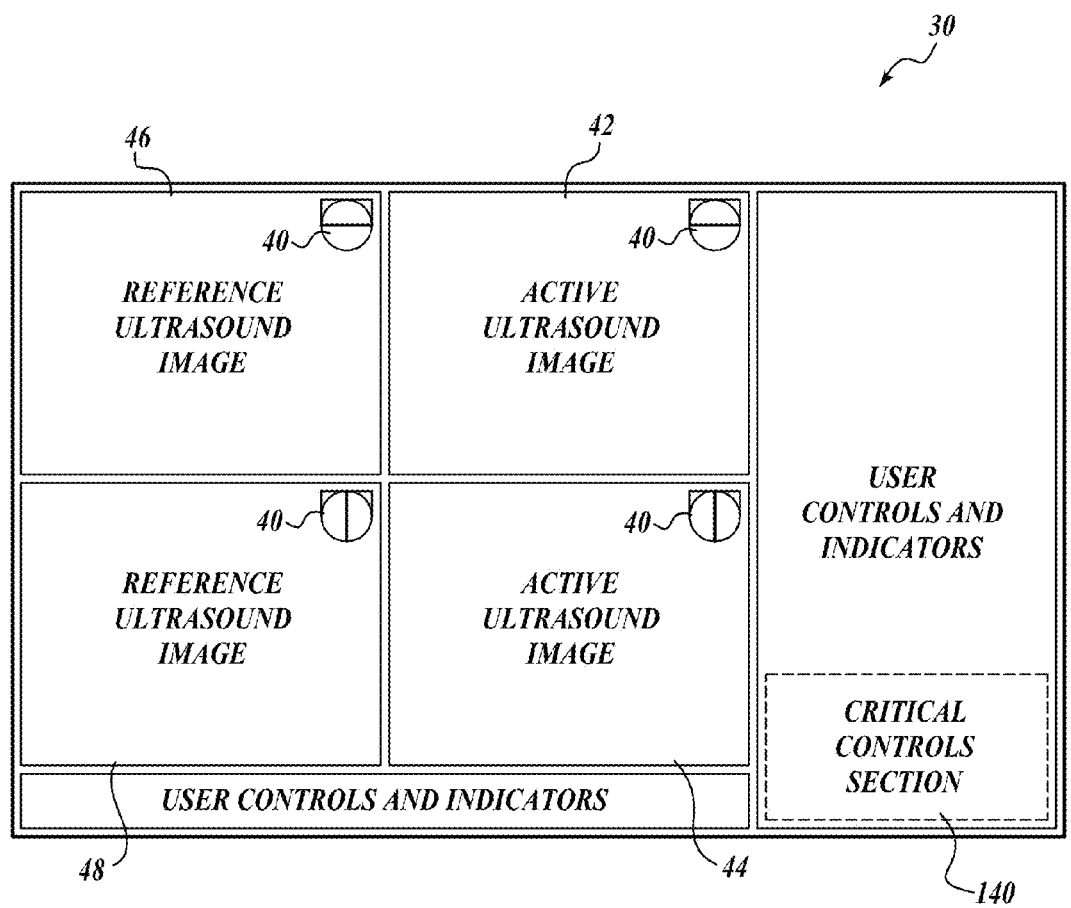
FIG. 14 illustrates a user interface layout including a screen layout with an alternative quad-view with critical controls section identified.
Figure 15:
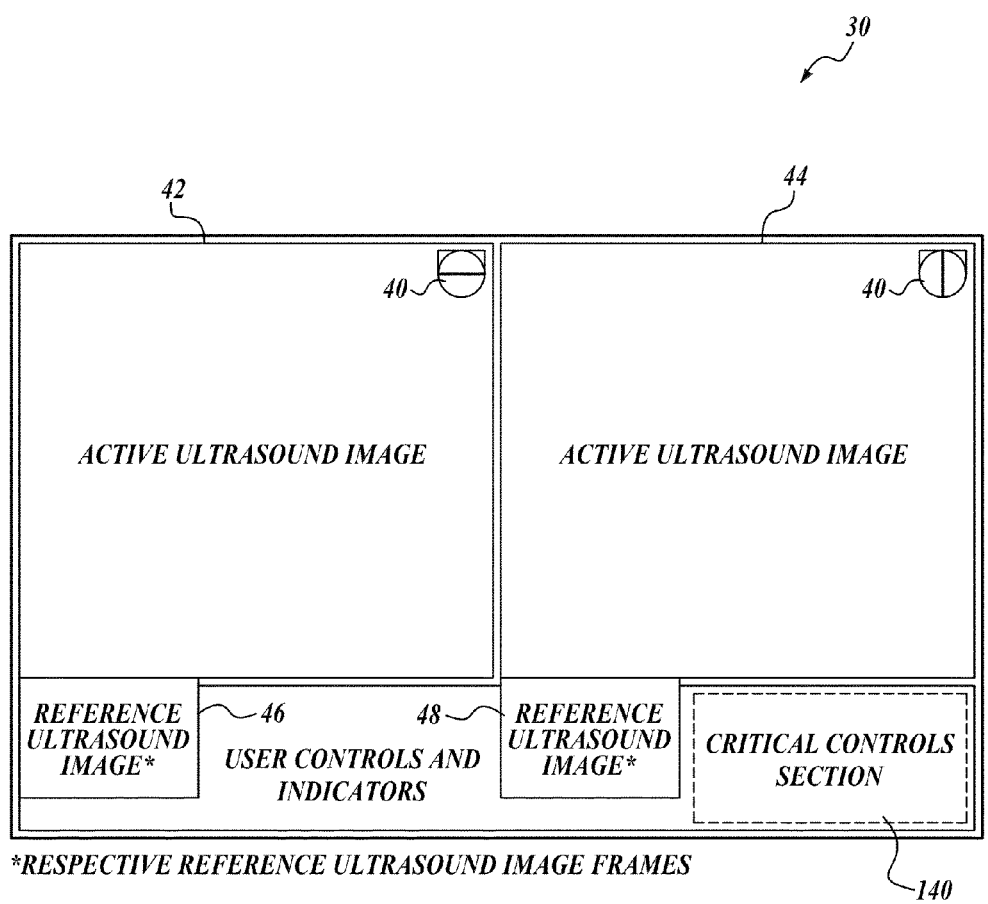
FIG. 15 illustrates a user interface layout including reference images overlaid on the screen.

In this embodiment, the two orthogonal image planes (active parallel frame 42 and active orthogonal frame 44) are always active and continually updated. Upon entry to the treatment mode (e.g., by activating the footswitch), the device 10 stores captured reference images in memory. If the user chooses to view the reference images (e.g., in case the user pauses treatment and needs to reposition), the user may select an icon to make the reference images visible. In at least one embodiment, the screen format of the user interface 30 may change to the aforementioned quad-view mode (see FIG. 14), with the critical control functions 140 remaining consistently placed and visible between the two formats. In an alternate embodiment, the screen format of the user interface 30 may remain constant and reference parallel frame 46 and reference orthogonal frame 48 may be overlaid on the screen of the user interface 30 (see FIG. 15).

In another embodiment, the user may select more than two active image planes. For example, one may choose to view four image planes equally spaced about the volume (e.g., 0, 45, 90, and 135 degrees) or about two opposing quadrants (e.g., 0, 22.5, 67.5, and 90 degrees), etc. In yet another embodiment, the display may include more than four image planes, for example with a relay out of the screen of the user interface 30 and/or with a larger display.

In the aforementioned image display formats, the user may have the option to also display the 360 degrees sweep view. In at least one embodiment, this may be accomplished by replacing the biplane view layout with a single-view 360-degree sweep layout. In another embodiment, the image display format may have a third view that is included with the two orthogonal views. This third view may have, in one embodiment, the 360-degree sweep view. In another embodiment, the third view could display a rendered 3D volume. In yet another embodiment, the third view could display a coronal plane view. In another embodiment, four images could be displayed with two orthogonal active images, an active 360-degree sweep, and the coronal view. It is recognized and appreciated that one can display four or more live images simultaneously where the displayed images are any combination of the aforementioned views (e.g., two orthogonal views, 360-degree swept view, coronal view, rendered 3D image, Doppler image, strain imaging image, and/or other standard imaging mode views).

As may be appreciated from the various implementations described herein, there are a variety of features and advantages obtained when constructing a device in accordance with the present disclosure. Furthermore, although the present disclosure has been described in connection with certain depicted implementations, those of ordinary skill will recognize that one or more features of a particular implementation described herein may be used in another implementation for similar advantage. Accordingly, it is not intended that the scope of the present disclosure in any way be limited by the precise forms described above, but instead be determined by reference to the claims that follow and equivalents thereto.

The embodiments of the invention in which an exclusive property or privilege is claimed are defined as follows:

1. A high intensity focused ultrasound (HIFU) system for real-time, image-guided HIFU treatment of tissue of a patient, the system comprising:
   a HIFU applicator configured to deliver HIFU energy to the tissue;
   a HIFU generator configured to control and transmit the HIFU energy through the HIFU applicator;
   an ultrasound imaging device that includes an imaging transducer, wherein during operation of the HIFU system, the imaging transducer is programmed to acquire imaging data providing (1) a real-time view of a first image plane that is parallel to a line passing through a feature of the HIFU applicator, wherein the feature of the HIFU applicator is moveable by an operator of the HIFU system to guide delivery of the HIFU energy to the tissue, and (2) a real-time view of a second image plane that is orthogonal to the first image plane, wherein the feature of the HIFU applicator visually provides to a user of the HIFU system a corresponding indication that correlates an orientation of a displayed image plane to the patient; and
   a user interface including a display, wherein the user interface displays images of the tissue on the display which provide three-dimensional visualization of the tissue, wherein the display simultaneously includes an active parallel frame depicting the real-time view of the first image plane parallel to the feature of the HIFU applicator and an active orthogonal frame depicting the real-time view of the second image plane orthogonal to the first image plane depicted in the active parallel frame.

2. The system of claim 1, wherein the user interface is further configured to display reference frames simultaneous with the display of the active parallel frame and the active orthogonal frame, wherein the reference frames include a reference parallel frame and a reference orthogonal frame, and wherein the reference parallel frame corresponds to the active parallel frame and provides a static view of the first image plane depicted in the active parallel frame, and the reference orthogonal frame corresponds to the active orthogonal frame and provides a static view of the second image plane depicted in the active orthogonal frame.

3. The system of claim 2, wherein the user interface is further configured to display one or more reference lines added to the image in the reference parallel frame or the reference orthogonal frame, and duplicate the one or more reference lines on the image in the corresponding active parallel frame or the corresponding active orthogonal frame, respectively.

4. The system of claim 1, wherein the user interface includes device controls for controlling the ultrasound imaging device, and wherein at least one of the device controls is a control icon accessible via the display.

5. The system of claim 4, wherein the system is configured to automatically set or adjust one or more of the device controls.

6. The system of claim 1, wherein the system is further configured to:
   detect and mark tissue boundaries;
   calculate and adjust treatment parameters based on the detected tissue boundaries; and
   display the marked tissue boundaries in one or more of the images on the display.

7. The system of claim 6, wherein the system is configured to automatically detect and mark the tissue boundaries, and automatically calculate and adjust the treatment parameters based on the detected tissue boundaries.

8. The system of claim 1, wherein the user interface is configured to display a 360-degree sweep view of the tissue.

9. The system of claim 1, wherein the ultrasound imaging device is connected to the system via a docking interface.

10. The system of claim 1, wherein the feature of the HIFU applicator includes handles that are operable by the user of the HIFU system to move the HIFU applicator, and wherein during motion of the HIFU applicator the first image plane remains parallel to the handles of the HIFU applicator.

11. A method of operation of a high intensity focused ultrasound (HIFU) system that includes a HIFU applicator, an ultrasound imaging device, and a user interface including a display, the method comprising:
   operating the ultrasound imaging device so as to acquire, during operation of the HIFU system, ultrasound images that include (1) a real-time view of a image plane that is parallel a line passing through a feature of the HIFU applicator, wherein the feature of the HIFU applicator is moveable by an operator of the HIFU system to guide delivery of HIFU energy, and (2) a real-time view of a second image plane that is orthogonal to the first image plane, wherein the feature of the HIFU applicator visually provides to a user of the HIFU system a corresponding indication that correlates an orientation of a displayed image plane to a patient being imaged; and displaying the ultrasound images the display of the user interface, wherein the display simultaneously includes an active parallel frame depicting the real-time view of the first image plane parallel to the feature of the HIFU applicator and an active orthogonal frame depicting the real-time view of the second image plane orthogonal to the first image plane depicted in the active parallel frame.

12. The method of claim 11, the method further comprising displaying reference frames simultaneous with display of the active parallel frame and the active orthogonal frame, wherein the reference frames include a reference parallel frame and a reference orthogonal frame, and wherein the reference parallel frame corresponds to the active parallel frame and provides a static view of the first image plane depicted in the active parallel frame, and the reference orthogonal frame corresponds with the active orthogonal frame and provides a static view of the second image plane depicted in the active orthogonal frame.

13. The method of claim 12, the method further comprising adding one or more reference lines to the image in the reference parallel frame or the reference orthogonal frame, and duplicating the one or more reference lines on the image in the corresponding active parallel frame or the corresponding active orthogonal frame.

14. The method of claim 11, the method further comprising controlling an ultrasound imaging device through device controls, wherein the ultrasound imaging device is used to display ultrasound images of the tissue on the user interface, and wherein at least one of the device controls is a control icon accessible on a display of the user interface.

15. The method of claim 14, the method further comprising automatically setting and adjusting one or more of the device controls.

16. The method of claim 11, the method further comprising detecting, marking, and displaying tissue boundaries, and calculating and adjusting treatment parameters based on the detected tissue boundaries.

17. The method of claim 16, the method further comprising automatically detecting, marking, and displaying tissue boundaries, and automatically calculating and adjusting treatment parameters based on the detected tissue boundaries.

18. The method of claim 11, the method further comprising displaying a 360-degree sweep view of the tissue.

19. The method of claim 11, the method further comprising selecting an icon on the user interface to cause reference images stored in a memory to be displayed, wherein the active parallel frame becomes a reference parallel frame that depicts a static image of the first image plane parallel to the feature of the HIFU applicator and the active orthogonal frame becomes a reference orthogonal frame that depicts a static image of the second image plane orthogonal to the image plane depicted in the reference parallel frame.

20. The method of claim 11, wherein the feature of the HIFU applicator includes handles that are operable by the user of the HIFU system to move the HIFU applicator, the method further comprising causing the first image plane to remain parallel to the handles of the HIFU applicator during motion of the HIFU applicator.

* * * * *

UNITED STATES PATENT AND TRADEMARK OFFICE
CERTIFICATE OF CORRECTION

PATENT NO. : 9,675,819 B2  
APPLICATION NO. : 13/943747  
DATED : June 13, 2017  
INVENTOR(S) : Lee David Dunbar et al.

Page 1 of 1

It is certified that error appears in the above-identified patent and that said Letters Patent is hereby corrected as shown below:

In the Claims

Column 12, Line 67 Claim 11:
"a real-time view of a image plane" should read, --a real-time view of a first image plane--.

Column 13, Line 11 Claim 11:
"displaying the ultrasound images the display" should read, --displaying the ultrasound images on the display--.

Signed and Sealed this
Thirty-first Day of December, 2019

Andrei Iancu
*Director of the United States Patent and Trademark Office*